United States Patent [19]

Duncan

[11] 4,257,422
[45] Mar. 24, 1981

[54] SURGICAL DRAIN

[75] Inventor: Patricia E. Duncan, Bayport, Minn.

[73] Assignee: Minnesota Mining and Manufacturing Company, St. Paul, Minn.

[21] Appl. No.: 20,437

[22] Filed: Mar. 14, 1979

[51] Int. Cl.³ ............................................ A61M 27/00
[52] U.S. Cl. .................... 128/350 R; 138/103; 138/118
[58] Field of Search .................. 128/348–351, 128/252, 276; 138/103, 118, 119

[56] References Cited

U.S. PATENT DOCUMENTS

| | | | |
|---|---|---|---|
| 1,510,571 | 10/1924 | Ware | 128/252 |
| 1,596,754 | 8/1926 | Moschelle | 128/350 R |
| 1,731,302 | 10/1929 | Erringer | 128/360 X |
| 1,928,992 | 10/1933 | Clark et al. | 138/103 |
| 3,430,631 | 3/1969 | Abramson | 128/350 |
| 3,957,054 | 5/1976 | McFarlane | 128/350 R |
| 4,131,399 | 12/1978 | Calvet | 138/118 X |
| 4,139,012 | 2/1979 | Zahorsky | 128/350 R |

OTHER PUBLICATIONS

Jackson–Internation. Surg., vol. 57, 1957 pp. 658–659 "Jackson-Pratt Brain Drain".

Primary Examiner—Dalton L. Truluck
Attorney, Agent, or Firm—Cruzan Alexander; Donald M. Sell; Gary L. Griswold

[57] ABSTRACT

The surgical drain tube of the present invention is comprised of a tubular member of a flexible pliable material. The tubular member has a oval exterior surface and a collapsible wall which defines a lumen which is normally of a substantially oval cross section. A tongue member is integrally formed with the inner surface of the top wall portion of the tubular member and extends the longitudinal length of the lumen. Oppositely deposed from the tongue member is a groove member which is formed integrally with the inner surface of the bottom wall portion of the tubular member and also extends the length of the passageway.

3 Claims, 2 Drawing Figures

SURGICAL DRAIN

This invention relates to a surgical drain.

Wound drain tubes are commonly used with a vacuum source to promote the removal of wound exudate post-operatively. This process encourages reapproximation of surgically incised tissues by eliminating standing fluid pockets thereby removing the potential places for infection to grow.

J. D. Moschelle in U.S. Pat. No. 1,596,754 discloses a drain tube which acts to remove the exudate by capillary flow utilizing the surface tension of the inner walls. The drain tube consists of a flexible thin wall tube having thick projecting ribs spaced equidistant along the internal surface. It has been found that when this thin wall tube is used with a more efficient vacuum source, the tube distorts resulting in the lateral displacement of the ribs. The resulting displacement allows the wall portion of the tube to collapse so as to mechanically occlude the flow of wound exudate from the wound site.

In an attempt to correct this mechanical occlusion, Frederick E. Jackson ("Jackson-Pratt Brain Drain," *International Surgery*, 57; 658–659, 1972,) suggests that the ribs be shaped as equilateral triangles with the apices jutting into the lumen of the drain and the base of the triangles integrally formed into the wall portion. The ribs are positioned on only one lateral wall of the rather oval cross section drain tube. The midlines of each rib are equidistant, so as to produce a uniform spacing between rib peaks. Under the influence of suction or external tissue pressure, the opposite drain tube wall approximates itself against these rib peaks, the intent being that of forming inter-rib spaces for fluid flow. The drain tube wall, adjacent and opposite the ribbed wall portion, is of uniform wall thickness.

Drains with these triangular ribs have been found to prematurely occlude in post-operative use, thus failing to remove the accumulated fluid as these drains are intended to do. This has been found to be the case even in the presence of substantial suction. This occlusion is believed to result from the abrupt angles and protrusions of the rib in the flow area which tend to produce viscus drag promoting flow stagnation and increasing the chances of clot formation. This premature occlusion may be further caused by an excess of wetted perimeter to flow area which has the tendency to lower the hydraulic radius of the drain.

Hydraulic radius of a channel, as used herein, is equal to the cross-sectional area of that part of the channel which is filled with fluid divided by the length of the wetted perimeter, *Perry Chemical Engineers Handbook* (4th Edition 1963).

The Applicant has developed a wound drain which minimizes the premature mechanical and clot occlusions which have been found to occur in the prior art devices. The surgical drain tube of the present invention is comprised of a tubular member of a flexible pliable material. The tubular member has a oval exterior surface and a collapsible wall which defines a lumen which is normally of a substantially oval cross section. A tongue member is integrally formed with the inner surface of the top wall portion of the tubular member and extends the longitudinal length of the lumen. Oppositely deposed from the tongue member is a groove member which is formed integrally with the inner surface of the bottom wall portion of the tubular member and also extends the length of the passageway. When the drain tube of the present invention is subjected to either edema or a vacuum when there are restrictions to flow, the tube flexes inwardly causing the tongue member to seat in the groove member forming normally open drainage lumens laterally deposed to the releasably joined groove and tongue members.

DETAILED DESCRIPTION OF THE PREFERRED EMBODIMENT

Figure 1:
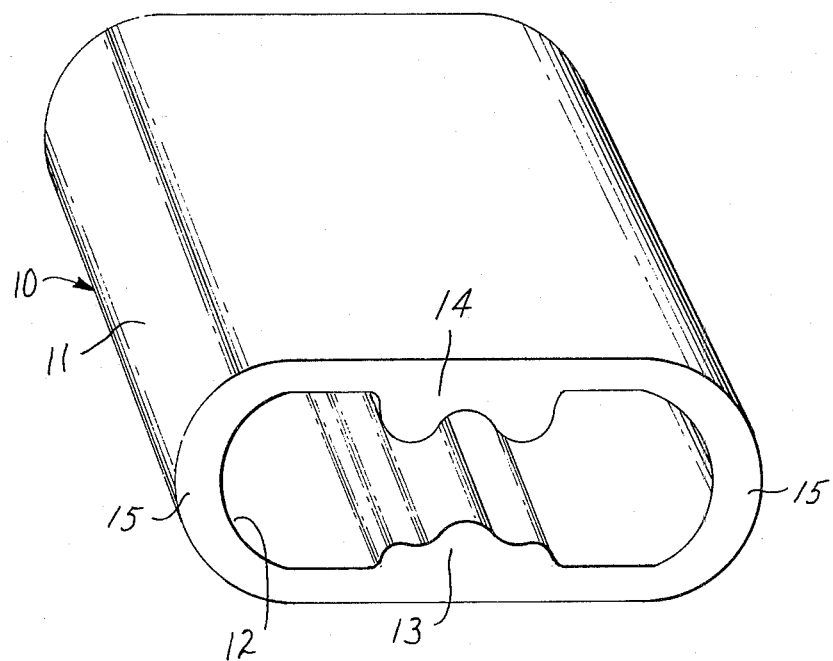
FIG. 1 is an enlarged perspective view of the surgical drain tube of the present invention.

Referring to the drawing wherein like reference characters designate like or corresponding characters and referring particularly to FIG. 1, the surgical drain 10 is comprised of tubular member 11 made of a soft supple material which is tissue compatible and non-adherent to the fibrous materials both internal and external to the drain. The preferred material for the drain of the present invention is silicone rubber. The external diameter and shape of tubular wall 11 should be selected so that the exit wound through which the drain passes is not excessively large and unattractive after healing. For the present invention the preferred cross section resembles an elongated oval. The tubular wall 11 defines a lumen 12 which passes through the entire tubular member 10. The lumen 12 preferably has a maximum oval shape of approximately 10 mm wide and 4 mm high. It is understood that other combinations of height and width may be utilized.

Integrally formed with the inner surface of the tubular wall 11 are tongue member 13 and an oppositely disposed groove member 14 both of which extend the longitudinal length of lumen 12. It is desirable that the ratio of the width of the lumen to the portions of tongue member 13 and groove member 14 which project into the lumen be about 10:3. The attainment of this ratio is believed to maximize the hydraulic radius which simultaneously increases the ability of the tube of the present invention to remove exudate from the body. It is preferred that portions of these integrally formed members protruding into the lumen 12 have all edges rounded. It has been found that such rounding reduces the flow resistance and minimizes the viscus drag which have been associated with both flow stagnation and the increasing propensity for occlusion from clot formations.

Figure 2:
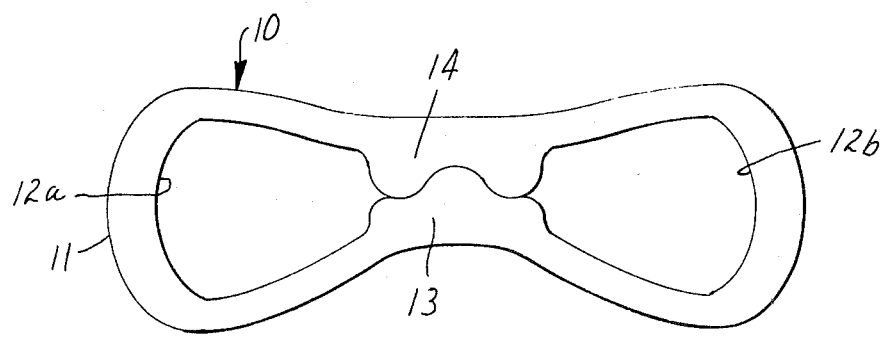
FIG. 2 is an end view of the surgical drain tube of the present invention flexing inwardly when operating under a condition of a vacuum restricted flow.

As best seen in FIG. 2, when the drain tube 10 is subjected to a vacuum and restricted flow, the tubular wall 11 flexes inwardly whereby the tongue member 13 seats in groove member 14 resulting in the formation of oppositely formed lumens 12a and 12b. This seating action of member 13 and 14 prevents the oppositely disposed portions of tubular wall 11 from lateral movement which would tend to occlude the entire drain. To further insure the integrity of the lumens 12a and 12b, the side tubular walls 15 are preferably 1.5 times as thick as that of the remaining portion of tubular wall 11 which are not integrally formed with tongue member 13 and groove member 14. It is contemplated that the surgical drain tube of the present invention could contain a plurality of tongue members 13 and groove members 14 so disposed that when the vacuum is drawn a plurality of lumens is formed.

In order to increase usefulness of the tube of the present invention for wound drainage, the wall portion 11 in the area of the oppositely disposed lumens 12a and 12b may contain a plurality of holes (not shown) through which the fluid can enter.

Surgical drain 10 may be made utilizing any of the methods generally known to the art, i.e. molding, extruding etc.

What is claimed is:

1. A surgical drain tube defined by a tubular member of a flexible and pliable material, said tubular member comprising a top wall portion, a bottom wall portion and side wall portions defining a lumen which is normally substantially oval in cross-section with said wall portions having an inner and outer surface, wherein said top wall portion has at least one tongue portion on the inner surface of said top wall portion extending substantially the length of said lumen and said bottom wall portion has at least one groove member on the inner surface of said bottom wall portion extending substantially the length of said lumen, said groove member disposed opposite said tongue member such that when a change in pressure occurs causing said lumen to collapse said tongue member releasibly seats in said groove member thereby forming a plurality of laterally disposed lumens, and wherein said side wall portions are thicker in cross-section than the thinnest region of said top wall portion and the thinnest region of said bottom wall portion.

2. A surgical drain tube defined by a tubular member of a flexible and pliable material, said tubular member comprising a top wall portion, a bottom wall portion and side wall portions defining a lumen which is normally substantially oval in cross-section, said wall portions having an inner and outer surface, wherein said side wall portions are thicker in cross-sectional thickness than said top wall portion and said bottom wall portion, and wherein said top wall portion has at least one tongue member attached to the inner surface of said top wall portion and extending substantially the length of said lumen and said bottom wall portion has at least one groove member attached to the inner surface of said bottom wall portion and extending substantially the length of said lumen, said groove member disposed opposite said tongue member such that when a change in pressure occurs causing said lumen to collapse said tongue member releasibly seats in said groove member thereby forming a plurality of laterally disposed lumens.

3. The surgical drain of claim 2 wherein the corner edges of the portions said groove member and said tongue member which project into said passageway are rounded.

* * * * *